(12) United States Patent
Robitaille et al.

(10) Patent No.: US 9,135,698 B2
(45) Date of Patent: Sep. 15, 2015

(54) SYSTEM AND METHOD FOR MEDICAL IMAGE INTENSITY STANDARDIZATION

(75) Inventors: Nicolas Robitaille, St-Augustin-de-Desmaures (CA); Simon Duchesne, Québec (CA)

(73) Assignee: UNIVERSITE LAVAL, Quebec, (CA)

( * ) Notice: Subject to any disclaimer, the term of this patent is extended or adjusted under 35 U.S.C. 154(b) by 0 days.

(21) Appl. No.: 13/807,892

(22) PCT Filed: Jul. 10, 2011

(86) PCT No.: PCT/IB2011/053067
§ 371 (c)(1),
(2), (4) Date: Dec. 31, 2012

(87) PCT Pub. No.: WO2012/007892
PCT Pub. Date: Jan. 19, 2012

(65) Prior Publication Data
US 2013/0101189 A1 Apr. 25, 2013

Related U.S. Application Data

(60) Provisional application No. 61/363,205, filed on Jul. 10, 2010.

(51) Int. Cl.
*G06T 7/00* (2006.01)
*G06T 5/00* (2006.01)
(Continued)

(52) U.S. Cl.
CPC .......... *G06T 7/0012* (2013.01); *G01R 33/5608* (2013.01); *G06T 5/007* (2013.01);
(Continued)

(58) Field of Classification Search
CPC ......... G06T 5/007; G06T 5/008; G06T 5/009; G06T 5/40; G06T 7/0012; G06T 2207/10088; G06T 2207/20128; G06T 2207/30016; G06K 9/4642; G06K 2209/051; G01R 33/5608; A61B 5/055; A61B 5/72
USPC .................. 382/128, 131, 274, 282, 283, 294
See application file for complete search history.

(56) References Cited

U.S. PATENT DOCUMENTS

2008/0292194 A1* 11/2008 Schmidt et al. ............... 382/217
2010/0259263 A1* 10/2010 Holland et al. ............... 324/310
2011/0286649 A1* 11/2011 Reisman et al. ............... 382/131

OTHER PUBLICATIONS

Robitaille et al., "Robust, large-scale intensity standardization of ADNI MRI dataset", Alzheimer's & Dementia: The Journal of the Alzheimer's Association, vol. 6, Issue 4, Supplement, p. S51, Jul. 4, 2010.*

(Continued)

*Primary Examiner* — Andrew W Johns
(74) *Attorney, Agent, or Firm* — Anglehart et al.

(57) ABSTRACT

Intensity standardization of MRI data sets aims at correcting scanner-dependent intensity variations. An automatic technique, called STI, which shares the simplicity and robustness of histogram-matching techniques, but also incorporates tissue spatial intensity information, has been discovered. The method comprises registering a medical image to a standard image; applying one or more masks to the medical and standard images for isolating certain specific image components; determining the most common intensity data pair between the medical and standard images for each isolated image component; calculating a formula that joins the most common intensity data pair of each image component; and interpolating an intensity data adjustment using the formula and applying it to the medical image data to generate a standardized version of the medical image.

19 Claims, 13 Drawing Sheets

(51) Int. Cl.
   *G06T 5/40* (2006.01)
   *G01R 33/56* (2006.01)
   *A61B 5/055* (2006.01)
   *A61B 5/00* (2006.01)

(52) U.S. Cl.
   CPC  *G06T 5/40* (2013.01); *A61B 5/055* (2013.01); *A61B 5/7264* (2013.01); *G06T 2207/10088* (2013.01); *G06T 2207/20128* (2013.01); *G06T 2207/30016* (2013.01)

(56) References Cited

OTHER PUBLICATIONS

Madabhushi et al., "Comparing MR Image Intensity Standardization Against Tissue Characterizability of Magnetization Transfer Ratio Imaging", Journal of Magnetic Resonance Imaging, vol. 24, Issue 3, pp. 667-675, Sep. 2006.*

Robitaille et al., "Tissue-Based Intensity Standardization Technique: Application to the ADNI Multi-Centric Dataset", Proceedings of the International Society for Magnetic Resonance in Medicine (ISMRM 2011), May 2011, 1 page.*

A Madabhushi et al., Comparing MR image intensity standardization against tissue characterizability of magnetization transfer ratio imaging, Journal of Magnetic Resonance Imaging, vol. 24 Issue 3, p. 667-675, Sep. 2006, abstract.

N, Robitaille et al., Robust, Large-Scale Intensity Standardization of ADNI MRI Dataset, Alzheimer's & Dementia: The Journal of the Alzheimer's Association, vol. 6 Issue 4, Supplement, p. S51, Jul. 4, 2010.

N. Robitaille et al., Tissue-Based Intensity Standardization Technique: Application to the ADNI Multi-Centric Dataset, Proccedings of the International Society for Magnetic Resonance in Medicine (ISMRM 2011), May 2011.

PCT/IB2011/053067 international preliminary report, dated Jan. 15, 2013.

PCT/IB2011/053067 international search report with claims 1-28, dated Dec. 7, 2011.

* cited by examiner

Site 1

Site 2

SYSTEM AND METHOD FOR MEDICAL IMAGE INTENSITY STANDARDIZATION

CROSS-REFERENCE

This application is the US national stage of International Patent Application No. PCT/IB2011/053067 filed on Jul. 10, 2011 which claims priority to U.S. provisional application no. 61/363,205 filed on Jul. 10, 2010.

TECHNICAL FIELD

The present invention relates generally to image intensity standardization. More specifically, the invention relates to methods and apparatuses for pre-processing and isolating specific components of a medical image for more efficient intensity standardization.

BACKGROUND

Magnetic resonance images (MRI) acquired with similar protocols but on different scanners will show dissimilar intensity contrasts for the same tissue types. These variations are machine-dependant, and go beyond random or systematic errors that can be corrected with image de-noising that are known in the art or bias field heterogeneity estimation. This situation is particularly acute in large, multi-centric settings such as the Alzheimer's Disease Neuroimaging Initiative (ADNI), in which data was acquired from 56 different centers in the United States and Canada. The ADNI was launched in 2003 by the National Institute on Aging, the National Institute of Biomedical Imaging and Bioengineering, the Food and Drug Administration, private pharmaceutical companies and non-profit organizations, as a $60-million, 5-year public-private partnership. It collected data on more than 800 subjects for Alzheimer's neuroimaging research.

Automated image-processing pipelines must be robust to these variations, if they are to provide reliable and reproducible measurements that have clinical meaning. Thus, intensity standardization must be performed so that similar intensities will have similar tissue meaning in the standardized images, regardless of scanner origin, location, type or operator. Techniques exist to perform standardization, but they are essentially aimed at matching the image histogram (i.e. from the image to be standardized) onto a standard or reference image histogram In particular, the technique of Nyul et al. [Nyul, L. G., J. K. Udupa, and X. Zhang, New variants of a method of MRI scale standardization. IEEE Trans Med Imaging, 2000. 19(2): p. 143-50.] matches percentile histogram landmarks (PCT), linearly interpolating intensities between them. Applicant's experience dictated that histogram matching should not be considered the unique objective, as it may artificially distort image contrasts and therefore result in a loss of biological meaning, quite exactly the opposite effect sought after. In some cases, two different tissue types can have a similar intensity profiles and therefore provide inefficient intensity adjustment and/or intensity adjustments that are not adapted to the specific tissue type. Indeed, intensity values alone do not inherently carry information about the tissue being observed. Rather, standardization should be aimed at matching spatially corresponding tissue intensities to remove, as much as possible, scanner effects. FIG. 1 shows a flowchart of a prior art methods for standardization.

One of the drawbacks of the prior art methods is that, in some cases, two different tissue types can have a similar intensity profiles (for example CSF and background), and therefore provide inefficient intensity adjustment and/or intensity adjustments that are not adapted to the specific tissue type.

SUMMARY

Applicants have discovered that intensity standardization is best achieved by matching spatially corresponding tissue intensities. Applicants present herein a novel automatic technique, called STI, which shares the simplicity and robustness of histogram-matching techniques, but also incorporates tissue spatial intensity information. Applicants compared STI to two histogram-matching techniques qualitatively, by visual inspection, and quantitatively, with four measures, on two multi-centric datasets, namely ADNI and a similar initiative called the European ADNI (E-ADNI). Qualitatively, STI showed better performance. This was reflected quantitatively by only one measure, the diagonal sum of the standard-vs.-input joint-histogram, suggesting that histogram-matching measures and techniques cannot be considered entirely appropriate.

It is therefore an object of the present invention to provide a new method of standardizing the intensity of a medical image to a standard image comprising pre-processing the medical image, registering the medical image to the standard image, applying one or more mask to the test and the standard images for isolating image components, determining the most common intensity data pair between the medical image and the standard image for each isolated image component, calculating a formula that joins the most common intensity data pair of each image component and interpolating an intensity data adjustment using the formula and applying it to the medical image data to generate a standardized version of the medical image.

In some embodiments of the present invention, a minimal and maximal data pair is added to provide a more precise intensity data interpolation in the lower and upper intensity values.

In yet other embodiments, a pre-processing step can comprise scaling, filtering, intensity heterogeneity correction, de-noising, re-sampling, smoothing and an intensity adjustment formula can comprise any one or combination of a linear, polynomial, basis-function (Gaussian, Bessel, Sine, Cosine, etc.) formula.

It is another object of the present invention to provide an apparatus for standardizing a medical image to a standard image comprising a medical image source and a standard image source, an image pre-processor for pre-processing the medical image, an image registrator for registering the medical image to the standard image, a component isolator for isolating specific image components, a data pair frequency selector for selecting the highest frequency intensity data pair, an intensity adjustment calculator for calculating a formula using intensity values of the data pairs and an intensity adjuster for adjusting the intensity data of the medical image In some embodiments of the apparatus, a visual display is utilized for presenting standardized images and in others, a transmitter is utilized for transmitting the standardized image data to another location or computer.

It is yet another object of the present invention to provide a method of determining a disease risk factor or of performing classification of an image comprising receiving an unstandardized image, standardizing said image according to the present invention and determining a disease risk factor or performing classification using said standardized image.

It is still another object of the present invention to provide a system for automatically calculating a disease risk factor or medical classification based on a medical image comprising a standardization apparatus according to the present invention and a calculator configured to process said standardized image to generate said disease risk factor or medical classification.

BRIEF DESCRIPTION OF THE DRAWINGS

The invention will be better understood by way of the following detailed description of embodiments of the invention with reference to the appended drawings, in which:

FIG. 8 (b) shows an original image for one subject at a specific MRI imaging site (site 1) in the E-ADNI study.

FIG. 8 (c) shows an original image for one subject at a specific MRI imaging site (site 1) in the E-ADNI study standardized according to PCT-1 method.

FIG. 8 (d) shows an original image for one subject at a specific MRI imaging site (site 1) in the E-ADNI study standardized according to PCT-10 method.

Fig. 8 (e) shows an original image for one subject at a specific MRI imaging site (site 1) in the E-ADNI study standardized according to STI method.

FIG. 9 (b) shows an original image for the same subject as that of FIG. 6 at another specific MRI imaging site (site 2) in the E-ADNI study.

FIG. 9 (c) shows an original image for the same subject as that of FIG. 6 at another specific MRI imaging site (site 2) in the E-ADNI study standardized according to PCT-1 method.

FIG. 9 (d) shows an original image for the same subject as that of FIG. 6 at another specific MRI imaging site (site 2) in the E-ADNI study standardized according to PCT-10 method.

FIG. 9 (e) shows an original image for the same subject as that of FIG. 6 at another specific MRI imaging site (site 2) in the E-ADNI study standardized according to STI method.

FIG. 12 (b) shows an image of white matter generated with fuzzy logic classification algorithms.

FIG. 12 (c) shows an image of cerebro-spinal fluid generated with fuzzy logic classification algorithms

DETAILED DESCRIPTION

Applicant's objective was to design an automated technique that would be simple and robust, while incorporating tissue-specific intensity information. Applicants herein report the development of a novel automated technique for Standardization of Intensities (STI), which makes use of spatial correspondences and available tissue masks from the standard image to adjust the intensity of the input image. STI was compared to one variant of Nyul et al., referred as PCT-10, and its modified form, referred as PCT-1, on two different multi-centric MRI datasets.

Figure 1:
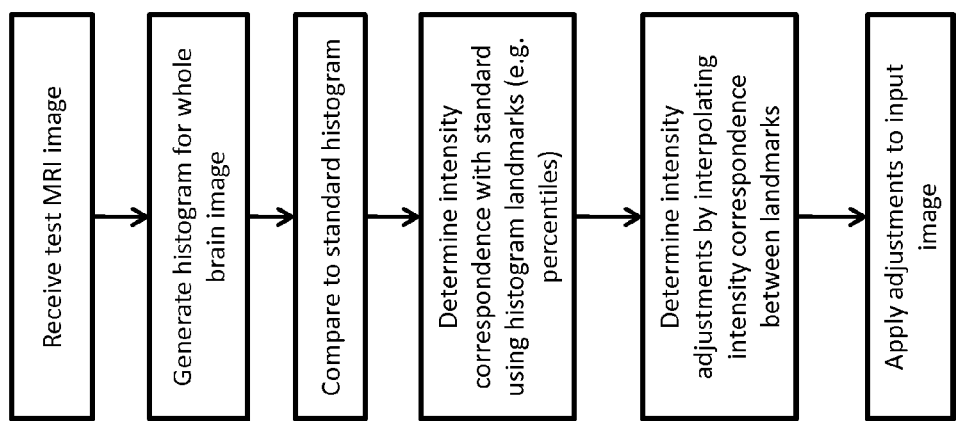
FIG. 1 is a flow chart illustration of a prior art method for image intensity standardization.
Figure 2:
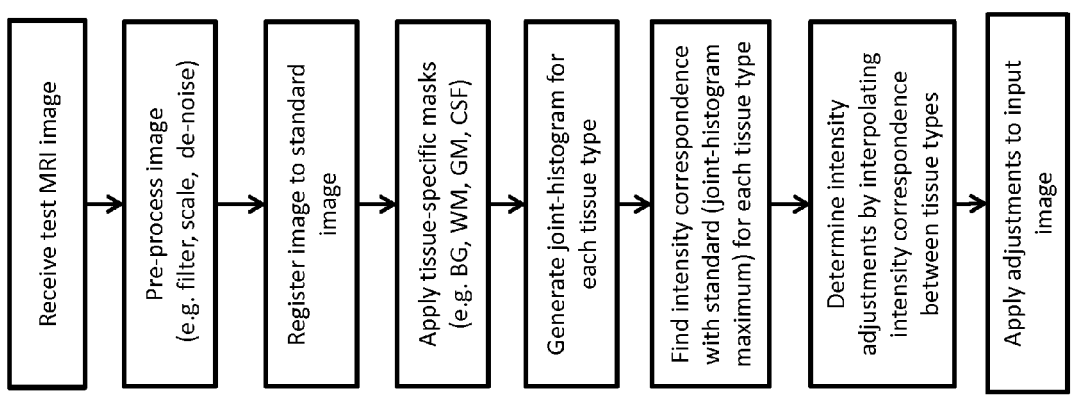
FIG. 2 is a flow chart illustration of a method for image intensity standardization according to the present invention.

FIG. 2 is a flowchart illustrating a method of image intensity standardization according to the present invention. The method comprises receiving a test MRI image, pre-processing image (e.g. filter, scale, de-noise), registering image to standard image, applying tissue-specific masks (e.g. BG, WM, GM, CSF), generating joint-histogram for each tissue type, finding intensity correspondence with standard (joint-histogram maximum) for each tissue type, determining intensity adjustments by interpolating intensity correspondence between tissue types and applying adjustments to input image.

In order to test out the new method on a real dataset, the European ADNI project (E-ADNI) dataset was obtained with permission. It consisted in data from three healthy volunteers, herein referred as Subjects 1 to 3 that acted as human quality control phantoms and that were scanned three times (scan; repeat scan, same session; rescan) within the span of few weeks at seven different European centers, herein referred as Sites 1 to 7, using the ADNI 3D T1-weighted MP-RAGE protocol taught by Jack et al. [Jack, C. R., Jr., et al., The Alzheimer's Disease Neuroimaging Initiative (ADNI): MRI methods. J Magn Reson Imaging, 2008. 27(4): p. 685-91]. In this study applicants used only the rescan data since scan and repeat scan were missing for one subject at one site. FIGS. 8 and 9 show the results obtained for Subject 1 at sites 1 and 2, respectively.

This dataset allowed the applicants to evaluate the performance of standardization techniques by avoiding inter-subject intensity variations and focusing only on inter-scanner differences. Making the reasonable hypothesis that subject tissue properties did not change between sites within the short study timeframe, a well-performing standardization technique should output the same tissue intensities independently of the scanning site.

The second dataset was obtained via ADNI. It consisted in 735 baseline MRIs from controls, mild cognitive impairment and probable Alzheimer's disease subjects, acquired on 56 different 1.5T scanners (GE Medical Systems; Siemens Healthcare; Philips Healthcare) using the aforementioned protocol of Jack et al. Data used in the preparation of this article were obtained from the ADNI database (www.loni.ucla.edu/ADNI). For up-to-date information see www.adni-info.org.

Pre-Processing

All MRI volumes were pre-processed in a similar fashion using the MINC image processing toolbox2: a) raw scanner intensity inhomogeneity correction; b) noise removal; c) linear scaling of grey level intensities to match the mean level of a target image; d) global registration (12 degrees of freedom) to the standard image space as taught by Collins et al. [Collins, D. L., et al., Automatic 3D Intersubject Registration of MR Volumetric Data in Standardized Talairach Space. Journal of Computer Assisted Tomography, 1994. 18: p. 192-205.], maximizing the mutual information between the two volumes; and e) resampling to a 1-mm3 isotropic grid. The standard image throughout this study was taken from BrainWeb [Aubert-Broche, B., A. C. Evans, and L. Collins, A new improved version of the realistic digital brain phantom. Neuroimage, 2006. 32(1): p. 138-45.] (normal brain, T1 image, 1-mm resolution, 0% noise, 0% non-uniformity). Global nonlinear registration to the standard image was also performed [D. L. Collins and A. C. Evans, "ANIMAL: Validation and Applications of Nonlinear Registration Based Segmentation," International Journal of Pattern Recognition and Artificial Intelligence, vol. 11, pp. 1271-1294, 1997 1997.] Hereafter, the pre-processed images will be referred to as the input images for the standardization techniques.). Intensity clamping can also be used in the pre-processing pipeline and involves setting to zero all intensity values below the percentile value 0.01, setting to 100 all intensity values above the percentile value 99.99, and linearly interpolating intensities between those limits. This step removes outliers of low and high intensities and rescales the image intensity between 0 and 100.

Intensity Standardization

Global registration established spatial correspondence between standard and input images, allowing applicants to compute a joint intensity histogram of the frequency distribution of intensity correspondences. From the most frequent tissue-specific correspondences, STI computed an intensity mapping function that mapped the input image onto the standard.

Since tissue intensities overlap, it was difficult to estimate tissue-specific correspondences from the global joint histogram. To refine its estimates, STI thus used available BrainWeb tissue masks for the background, white matter and grey matter. For each tissue, STI performed the following steps:

1. Mask both input and standard images, i.e. keep only the voxels contained in the tissue mask.
2. From the masked voxels, compute and smooth (with a Gaussian low-pass filter for example), the standard-vs.-input joint intensity histogram.
3. Find the two-dimensional (2D) position of the maximum in the joint histogram. The maximum corresponds to the most frequent intensity correspondence (intensity data pair) between the input and standard images for the current tissue. The 2D coordinates correspond to the intensity values of the input and standard images. Applicants supposed that this point corresponds to the input-to-standard intensity mapping for the current tissue.

The 2D intensity points obtained for each tissue were used as control points in the mapping function. To this set, STI added two extra points: the first (0,0) mapped both minimum intensities in the input and standard images, and the second (100,100), the maximum values. STI finally completed the mapping function by linearly interpolating intensities between the 2D points.

Applicants compared STI to the histogram-matching technique described in Nyul et al. as L4, which uses percentile landmarks spaced by 10%. Herein, the technique is referred as PCT-10. Applicants also compared STI to a modified version using landmarks spaced by 1% for better histogram matching. This technique is herein referred as PCT-1.

Comparison Measures

Applicants first visually inspected all standardized images and qualitatively compared the standardization techniques. The problem was then to define a measure that applicants could use to perform a quantitative comparison. Since applicants think that standardization should aim at matching corresponding tissue intensities, applicants needed measures that would evaluate both histogram matching and spatial intensity correspondence. Applicants thus performed a comparison based on the following four measures:

1. Kullback-Leibler divergence (KLD) with respect to standard. Applicants used KLD to evaluate histogram matching. It measures the difference between the histograms of the standardized and the standard images. KLD does not depend on spatial correspondence.
2. Mean absolute error (MAE), with respect to standard, i.e. mean absolute intensity difference between the standardized and the standard images over the entire image volume. MAE depends on spatial correspondence between the standard and the input images.
3. Normalized mutual information with respect to input (NMI) as shown in Studholme et al. [Studholme, C., D. L. G. Hill, and D. J. Hawkes, An overlap invariant entropy measure of 3D medical image alignment. Pattern Recognition, 1999. 32(1): p. 71-86]. Although NMI does not assess standardization performance, applicants used that measure to evaluate how the standardization affects the input image. As NMI decreases, information is lost in the standardization process.
4. Joint-histogram diagonal sum with respect to standard (JHDS), i.e. the sum of the diagonal bins of the joint histogram of standard vs. standardized images. Applicants note that the bin size corresponded to a 1% intensity variation. The rationale behind this proposed measure is that the joint histogram of the standard vs. input images should present higher frequencies on its diagonal after standardization. Ideally, if the standardization was perfect, the joint histogram would be concentrated on the diagonal only, mapping each intensity value of the input image to the same value for the standard image. JHDS depends on spatial correspondence between the standard and the input images.

By visual inspection of the E-ADNI dataset, STI gave overall the best results, followed by PCT-1 and PCT10, on the E-ADNI dataset (a complete set of drawings is publicly available at the following permanent web link: http://medics.crulrg.ulaval.ca/

FIG. 8 shows the standardized images for Subject 1 at site 1 and FIG. 9 shows the standardized images for Subject 1 at site 2 using the three techniques. For the most challenging cases, Sites 6 and 7, STI showed the best performance, while PCT-10 and PCT-1 underestimated the white matter intensity for Site 6 and overestimated it for Site 7. Applicants obtained similar results for Subjects 2 and 3. It will be appreciated that interpretation of these images is facilitated by viewing on a single page and on a color scale. However, for the purposes of this application, all images where transformed to grey scale. The spatial coordinates for all images of FIGS. 8 and 9 are (x,y,z; 0,−18,18).

Table 1 presents the quantitative results of the four measures obtained for the standardizations of FIG. 8. Unsurprisingly, PCT-1 gave the lowest KLD values in all cases, showing that it is the best histogram-matching technique.

However, STI gave overall the best results for MAE and JHDS. As for NMI, PCT-1 gave the poorest values.

TABLE 1

KLD, MAE, NMI, and JHDS measures obtained for the seven images (Site 1 to 7) acquired on Subject 1 and shown in FIG. 8 in the E-ADNI dataset. Best scores are highlighted in bold characters. Referring to FIG. 8, JHDS reflects the qualitative evaluation.

| Measure | Method | Site 1 | Site 2 | Site 3 | Site 4 | Site 5 | Site 6 | Site 7 |
|---|---|---|---|---|---|---|---|---|
| KLD | Original | 0.344 | 0.253 | 0.226 | 0.184 | 0.138 | 0.742 | 0.560 |
|  | PCT-10 | 0.128 | 0.074 | 0.094 | 0.067 | 0.084 | 0.045 | 0.103 |
|  | PCT-1 | 0.003 | 0.007 | 0.047 | 0.002 | 0.066 | 0.028 | 0.009 |
|  | STI | 0.163 | 0.136 | 0.073 | 0.119 | 0.115 | 0.095 | 0.141 |
| MAE | Original | 0.080 | 0.085 | 0.072 | 0.075 | 0.072 | 0.082 | 0.093 |
|  | PCT-10 | 0.070 | 0.078 | 0.071 | 0.074 | 0.071 | 0.075 | 0.082 |
|  | PCT-1 | 0.072 | 0.076 | 0.070 | 0.074 | 0.071 | 0.075 | 0.077 |
|  | STI | 0.066 | 0.074 | 0.066 | 0.073 | 0.070 | 0.077 | 0.071 |
| NMI | Original | 1 | 1 | 1 | 1 | 1 | 1 | 1 |
|  | PCT-10 | 0.876 | 0.867 | 0.899 | 0.878 | 0.882 | 0.868 | 0.862 |
|  | PCT-1 | 0.861 | 0.863 | 0.891 | 0.876 | 0.882 | 0.863 | 0.860 |
|  | STI | 0.860 | 0.874 | 0.925 | 0.858 | 0.884 | 0.866 | 0.874 |
| JHDS | Original | 0.128 | 0.155 | 0.120 | 0.111 | 0.176 | 0.062 | 0.092 |
|  | PCT-10 | 0.117 | 0.145 | 0.157 | 0.112 | 0.157 | 0.152 | 0.126 |
|  | PCT-1 | 0.116 | 0.150 | 0.159 | 0.115 | 0.159 | 0.151 | 0.129 |
|  | STI | 0.154 | 0.171 | 0.177 | 0.131 | 0.170 | 0.158 | 0.163 |

Qualitatively, STI gave again better results overall for the ADNI dataset, followed by PCT-1 and PCT-10. Applicants provide three image examples for qualitative evaluation at http://medics.crulrg.ulaval.ca/. Focusing on PCT-10 and PCT-1, the white matter intensity was underestimated in (A), while it was overestimated in (B) and (C). Applicants also note that the cerebrospinal fluid (CSF) intensity was overestimated for all three images, especially in (B) and (C). For the three cases, STI gave the best results. In particular, applicants note that the CSF intensity was kept similar to the original image and background of the standard.

Quantitative results obtained for the three examples above followed the same trend as for the whole ADNI dataset. In Table 2, applicants show the mean and standard deviation of KLD, MAE, NMI and JHDS for the whole dataset. PCT-1 gave the best results for KLD and MAE, followed by PCT-10. STI showed better NMI and JHDS, matching applicant's visual, qualitative evaluation. Applicants also performed two-sample t-tests between standardization methods for each measure. Distributions were all significantly different (p-value <0.001), except for one case: between PCT-10 and PCT-1, JHDS distributions were not, with a p-value of 0.439.

TABLE 2

Mean and standard deviation, in parentheses, of KLD, MAE, NMI and JHDS measures obtained for the whole ADNI dataset. Best scores are highlighted in bold characters.

| Method | KLD | MAE | NMI | JHDS |
|---|---|---|---|---|
| PCT-10 | 0.065 (0.026) | 0.077 (0.005) | 0.867 (0.012) | 0.142 (0.014) |
| PCT-1 | 0.013 (0.024) | 0.076 (0.004) | 0.860 (0.014) | 0.141 (0.015) |
| STI | 0.160 (0.055) | 0.079 (0.005) | 0.885 (0.017) | 0.167 (0.012) |

According to the KLD measure, PCT-1 was better than STI, showing superior histogram matching. However, as shown qualitatively in FIG. 8, STI showed better spatially-distributed intensity matching. For MAE, STI showed the best scores overall with the E-ADNI dataset, but the worst with the ADNI dataset. Those results suggest that KLD and MAE measures, along with histogram-matching techniques, cannot be considered entirely appropriate.

In fact, one of applicants' main challenges was to determine which measure to use to assess standardization technique performances. One objective in finding such a measure would be to use an optimization method to find a better intensity mapping function.

While NMI suggested that more information from the input image was kept for STI than for PCT-1 or PCT-10 with the ADNI dataset, this measure cannot be used for that purpose since it compares the standardized image with the input image, not with the standard.

JHDS seemed to follow best applicants' qualitative evaluation by visual inspection. Those results lead the applicants to believe that it is a first step toward an appropriate performance measure.

Although a limitation of STI is that global linear registration is necessary, visual inspection showed that STI performed better than PCT-10 and PCT-1. With this new technique, applicants were able to successfully standardize intensities in two multi-centric datasets.

Figure 3:
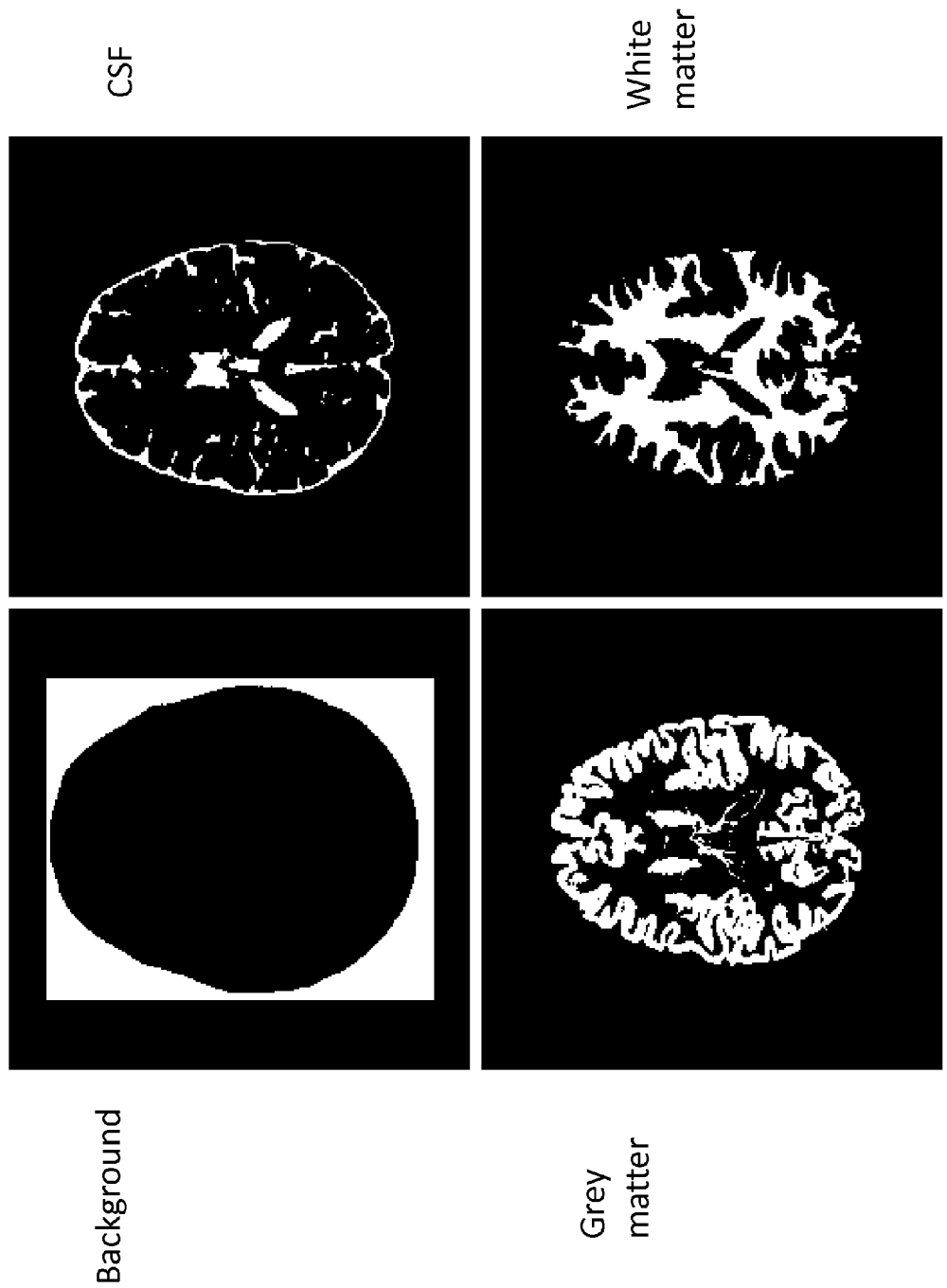
FIG. 3 shows sample masks used for isolating various image components such as grey matter, white matter, CSF and background

It will be understood that a "mask" of an image component allow to isolate specific areas of the image which can correspond to specific tissue types such as grey matter, white matter, CSF and background. It will be appreciated in FIG. 3 that the image components being masked are those in white. Any pixel/voxel not appearing in the mask is discarded and any pixel/voxel from the test image and standard image corresponding to the location of a pixel/voxel in the mask will be retained for further analysis such as generating joint histograms. In this case, applicants used brain masks obtained from the McGill Brain Imaging Center.

Registration is the process of identifying the transformations (rotation, translation, scaling, etc) that maximize the cross-correlation between characteristics from the standard and test images, estimated at each pixel/voxel position.

Figure 4:
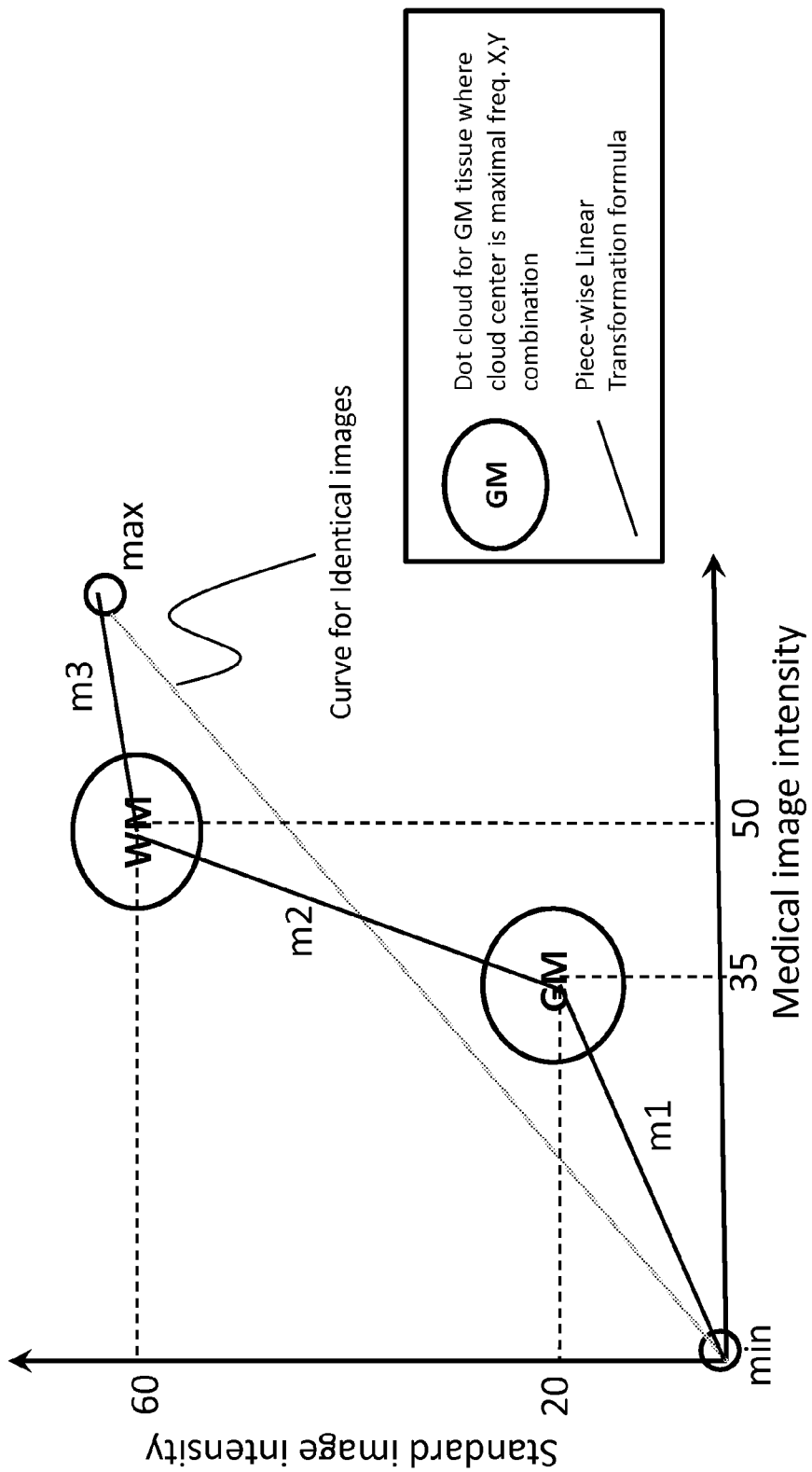
FIG. 4 is an illustrative example of the intensity adjustment method of the present invention using a joint histogram approach for each tissue type and interpolating intensity correspondence between tissue types in piece-wise linear fashion.

FIG. 4 schematically illustrates intensity adjustment of a medical image according to the present invention. A dot plot joint-histogram of medical image intensity (x axis) and standard image intensity (y axis) for each pixel/voxel is presented. Sample dot clouds for grey matter and white matter are provided. If two identical images were compared with this method, a line with a slope (m) of 1 and a y-intercept (b) of 0 would be obtained. In this example,
if X is less than intensity 35, $y=m1x+b1$,
if X is between 35 and 50, $y=m2x+b2$
if X is greater than 50, $y=m3x+b3$
where b is the y-intercept and m is the slope of the line (formula).

A specific linear formula of the type $y=mx+b$ is used. The "adjusted" intensity (y value) for any medical image intensity (x value) depends on the value of X and its proximity to a tissue component. For example, if the intensity value of the pixel/voxel of the medical image to be standardized is 30, then the formula used will be $y=m1x+b1$. However, if the intensity value of the pixel/voxel of the medical image to be standardized is 60, then the formula used will be $y=m3x+b3$, and so on. It will be appreciated that the more image components in a medical image, the more formulas will be used to "adjust" the medical image intensity value. It will be understood by those skilled in the art the formula need not be a linear formula it could also be, for example, a polynomial formula. As discussed above, minimum and maximum data points were added. In this example, the presence of two image components would allow to generate only one linear formula that would not be efficient for low or high intensity values. By adding the minimum and maximum points, the "adjustment" to low and high values generates a more useful standardized image.

In cases where only 1 image component is used (i.e. one mask isolates one tissue type and all other tissues are discarded from the image), having the minimum and maximum allows to calculate 2 linear formulas. Without these added points, it would not be possible to provide an intensity adjustment factor.

Figure 5A:
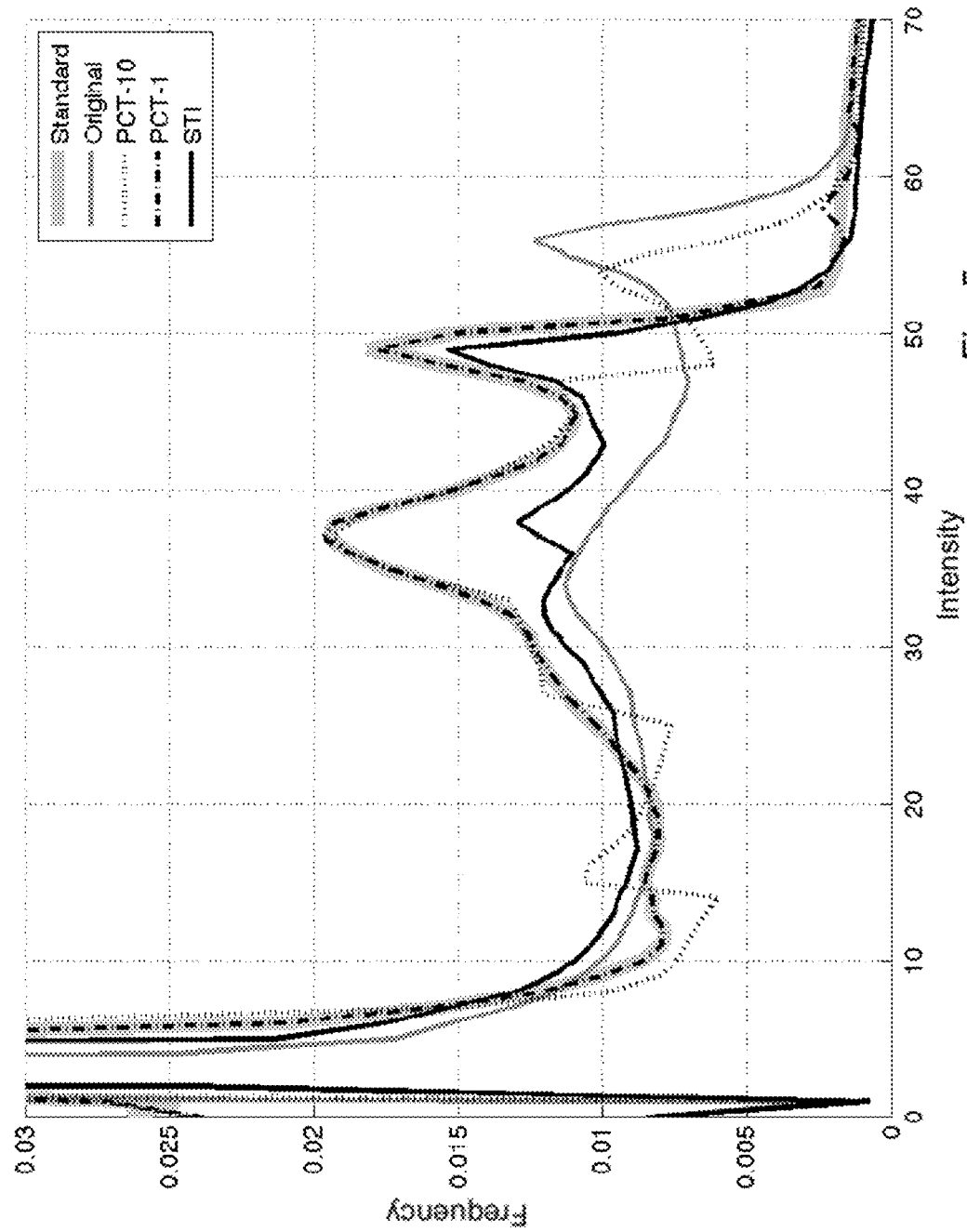
FIG. 5a shows an example of an intensity histogram after standardization by the various methods indicated (PCT-10, PCT-1, STI).
Figure 5B:
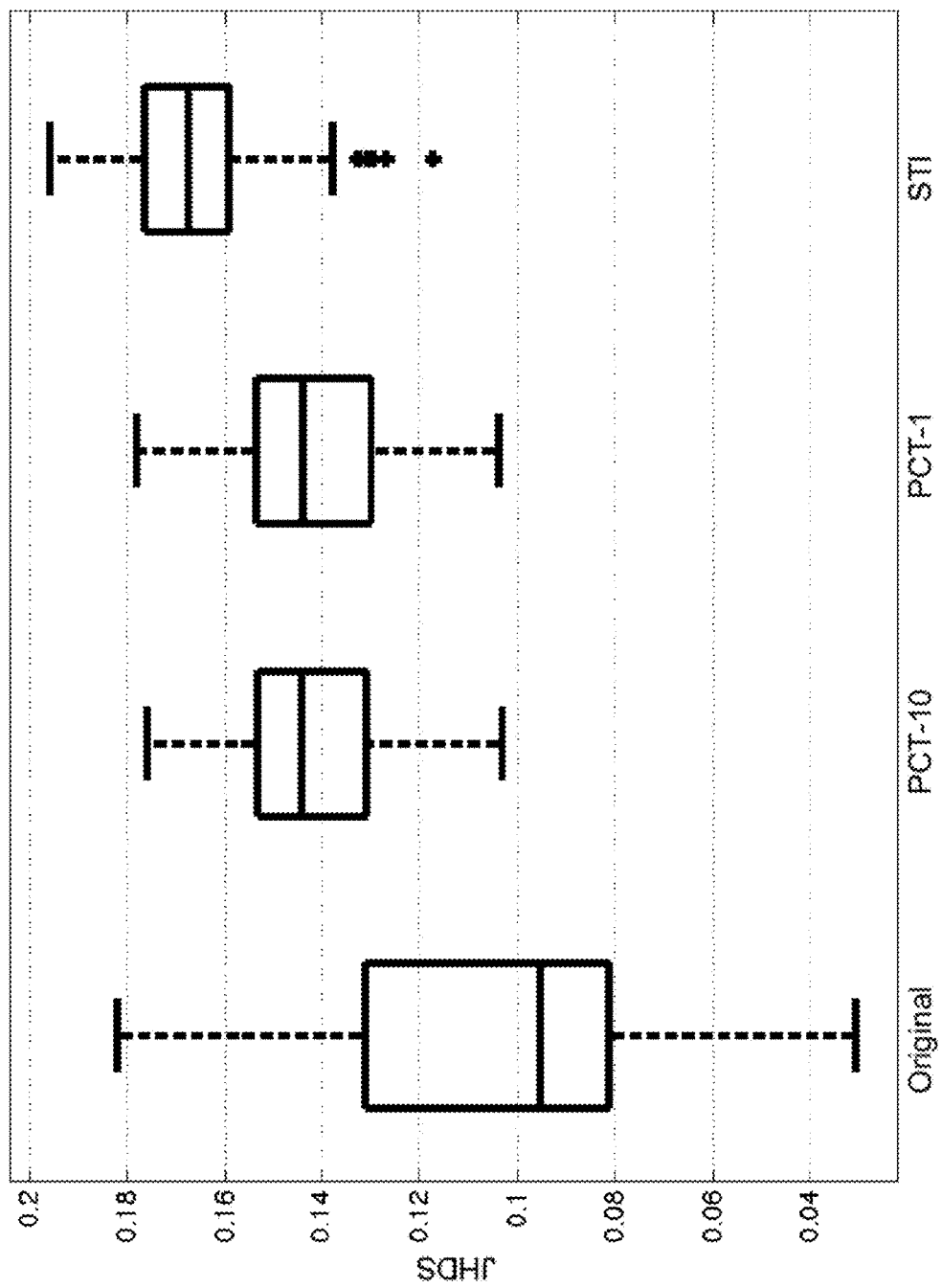
FIG. 5b shows a measure used to determine standardization method effectiveness (in this case, JHDS).

FIG. 5 shows an example of an intensity histogram after standardization by the various methods indicated (PCT-10, PCT-1, STI) as well as one of the statistical measures (JHDS) used to determine standardization method effectiveness.

Figure 6:
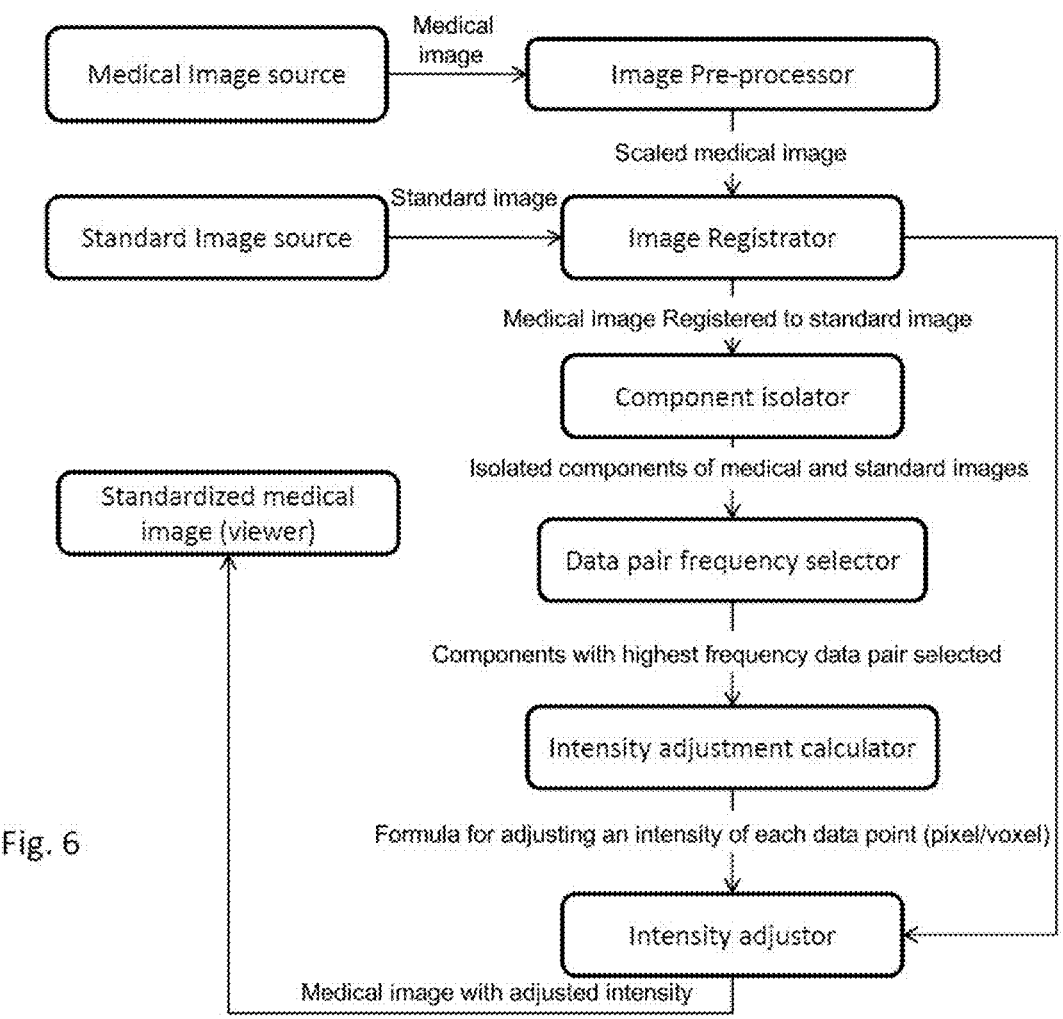
FIG. 6 is a block diagram illustrating various components of an apparatus for image intensity standardization.

FIG. 6 is a block diagram illustrating various components of an apparatus for image intensity standardization. In such an apparatus, a source of medical images and a source of standard images are required. An image pre-processor pre-processes the medical image to facilitate its registration by the registrator. Masking specific tissues with the component isolator is an essential part of the present invention. Once tissues are isolated, the highest frequency data pair is retained for each tissue and used in the intensity adjustment calculator which generates an "adjustment factor" to be applied to all pixels/voxels of the medical image as a function of their proximity to the high frequency data pair. Once adjusted or standardize, the image can be presented on a viewer or image data can be transmitted to another location/computer. It will be appreciated that most aspects of this diagram can be performed by a computer using software programmed to carry out the described method.

Figure 7:
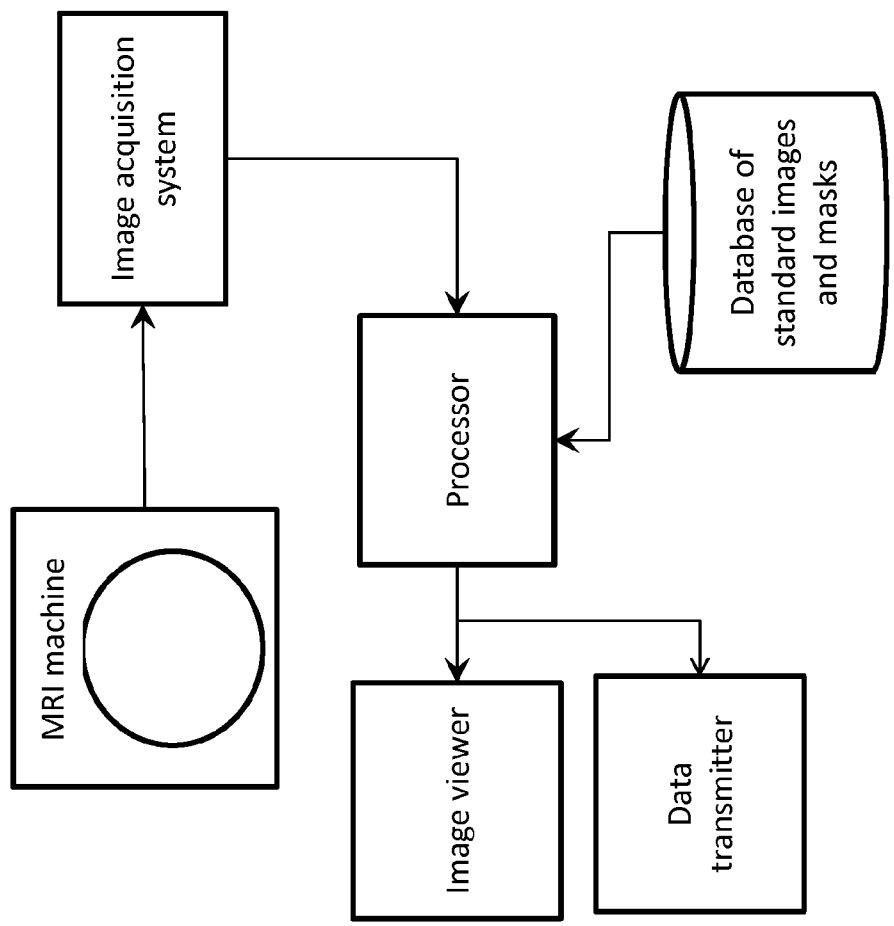
FIG. 7 is a block diagram illustrating one possible physical setup of the present invention.
Figure 8E:
FIG. 8 (a) shows a standard image for one subject at a specific MRI imaging site (site 1) in the E-ADNI study.
Figure 8E:
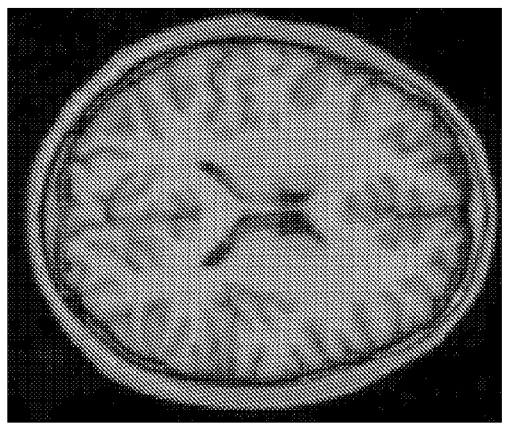
Figure 8B:
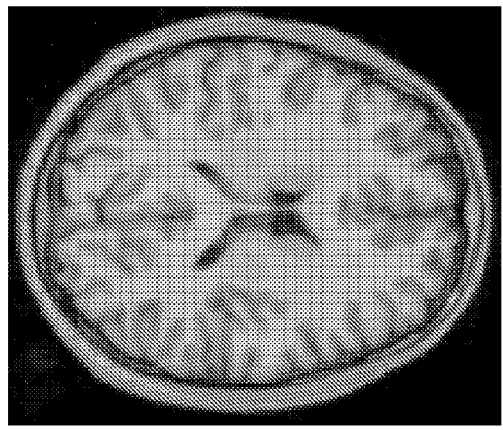
Figure 8D:
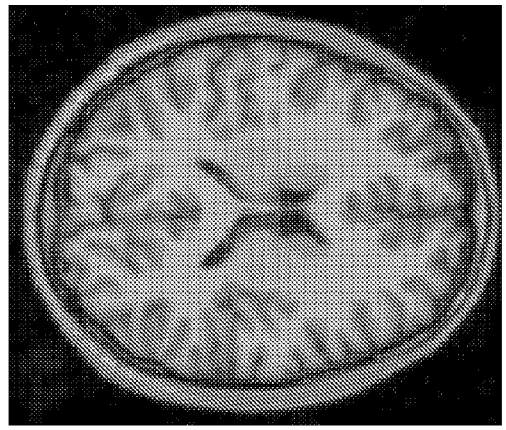
Figure 8A:
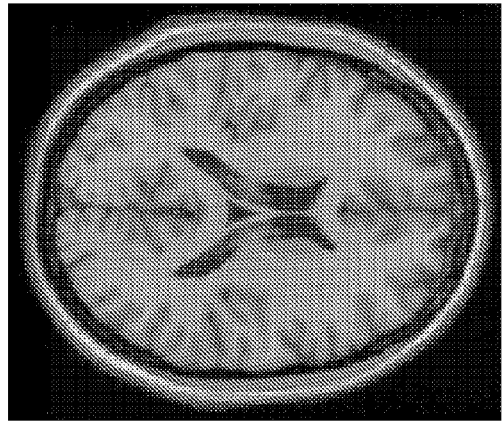
Figure 8C:
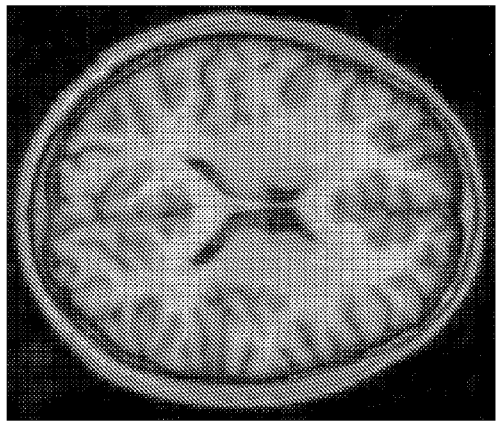
Figure 9B:
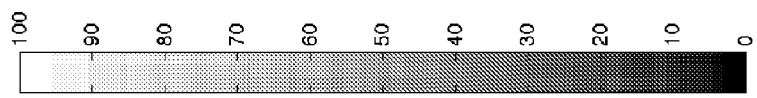
FIG. 9 (a) shows a standard image for the same subject as that of FIG. 6 at another specific MRI imaging site (site 2) in the E-ADNI study.
Figure 9B:
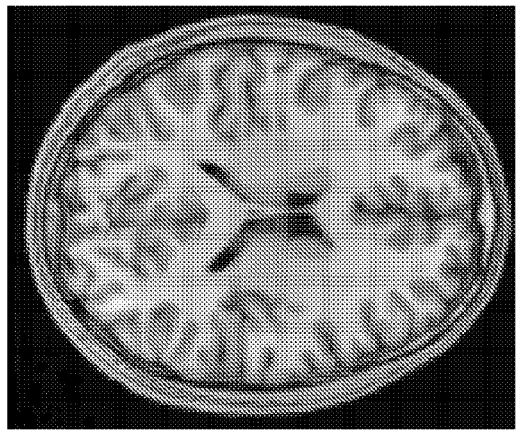
Figure 9A:
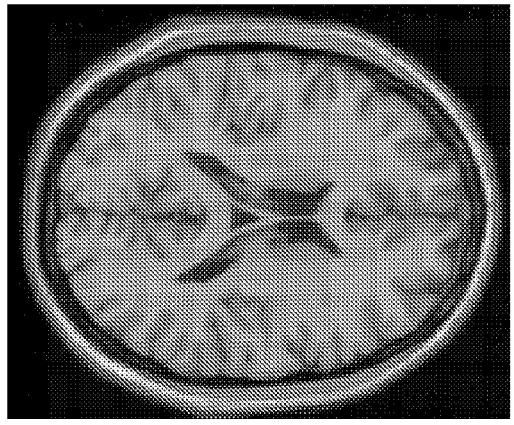
Figure 9E:
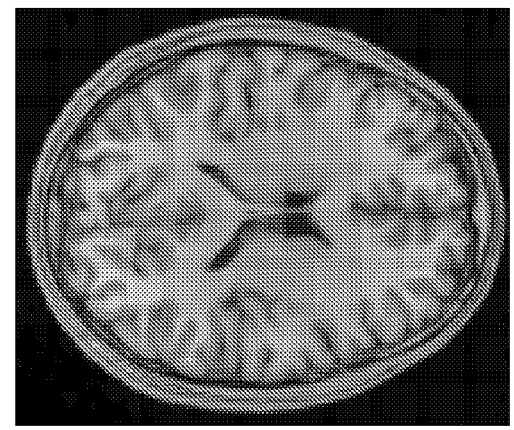
Figure 9D:
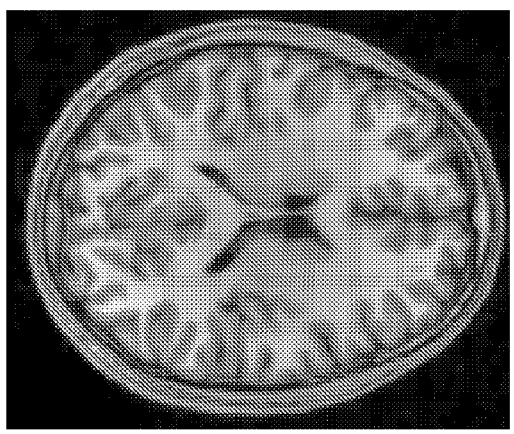
Figure 9C:
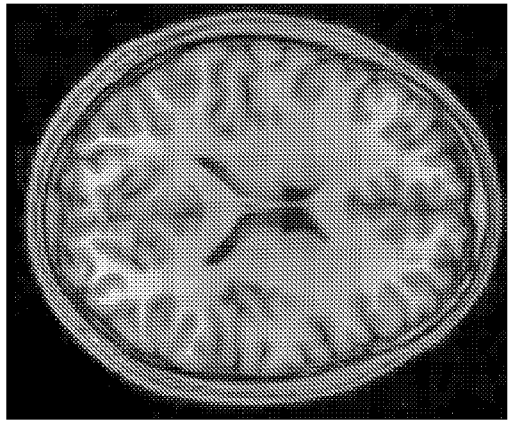

FIG. 7 is a block diagram illustrating one possible physical setup of the present invention. In this setup, a subject is placed inside an MRI machine for generating an image of his brain. In this case the imaging is performed by radio frequency emitters/sensors that are placed inside the MRI machine. The RF sensors can send data to an image capture device for generating a viewable image of the brain. The image thereby generated must be pre-processed. After pre-processing, the image is ready to be registered with a standard image representing the same "brain volume" obtained from an image database. After registration of the image to the standard image, masks are applied in order to isolate specific tissue types. These masks can also be obtained from a mask database. A processor/calculator determines the adjustment to be performed as a function of intensity and prepares a standardized image that can be viewed on an image viewer or transmitter with a data transmitter.

FIG. 8 shows images for one subject at a specific MRI imaging site in the E-ADNI study where a standard image (a), an original image (b) and an original image standardized according to PCT-1 (c), PCT-10 (d), and STI (e) methods are presented. This is to provide an example and highlight the effectiveness of the STI approach for intra-subject variability on different imaging devices (in this case MRI machine).

FIG. 9 shows images for the same subject as that of FIG. 6 at another specific MRI imaging site in the E-ADNI study where a standard image (a), an original image (b) and an original image standardized according to PCT-1 (c), PCT-10 (d), and STI (e) methods are presented. This is to provide an example and highlight the effectiveness of the STI approach for intra-subject variability on different imaging devices (in this case MRI machine).

It will be appreciated that not all images corresponding to the statistical results of table 1 are shown herein. Selected examples for two of the seven sites tested are shown in FIGS. 8 and 9 and these images correspond to sites 1 and 2. A complete set of drawings, including those corresponding to table 2 are publicly available at the following web link:

http://medics.crulrg.ulaval.ca/

Figure 10:
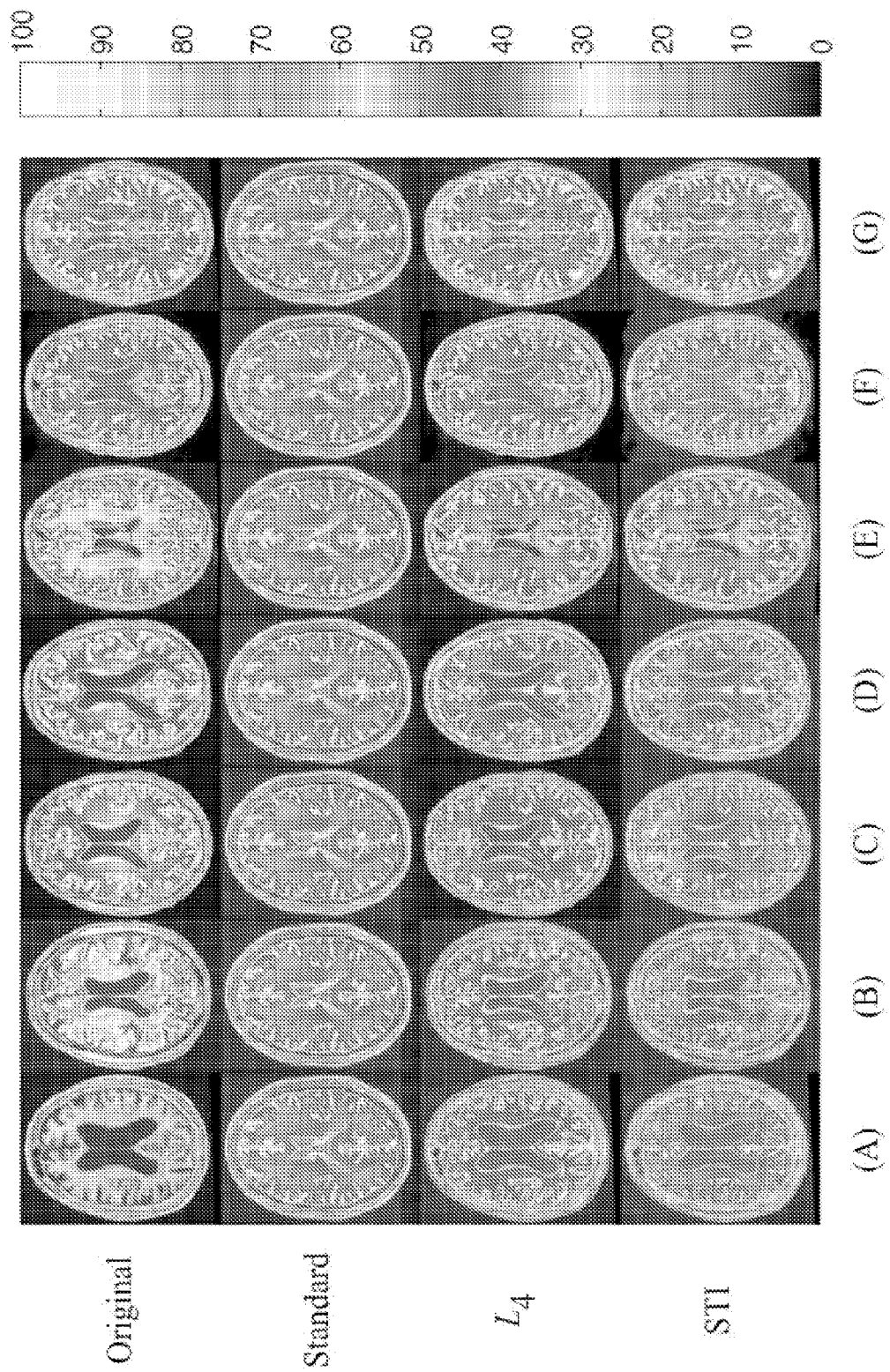
FIG. 10 shows images of the ADNI dataset, sorted according to MAE percentiles (A) 100, (B) 90, (C) 75, (D) 50, (E) 25, (F) 10 and (G) 0 obtained for the foreground voxel set with $L_4$. Images (A) and (G) correspond respectively to the highest (worst) and lowest (best) MAE obtained in the foreground for $L_4$.
Figure 11:
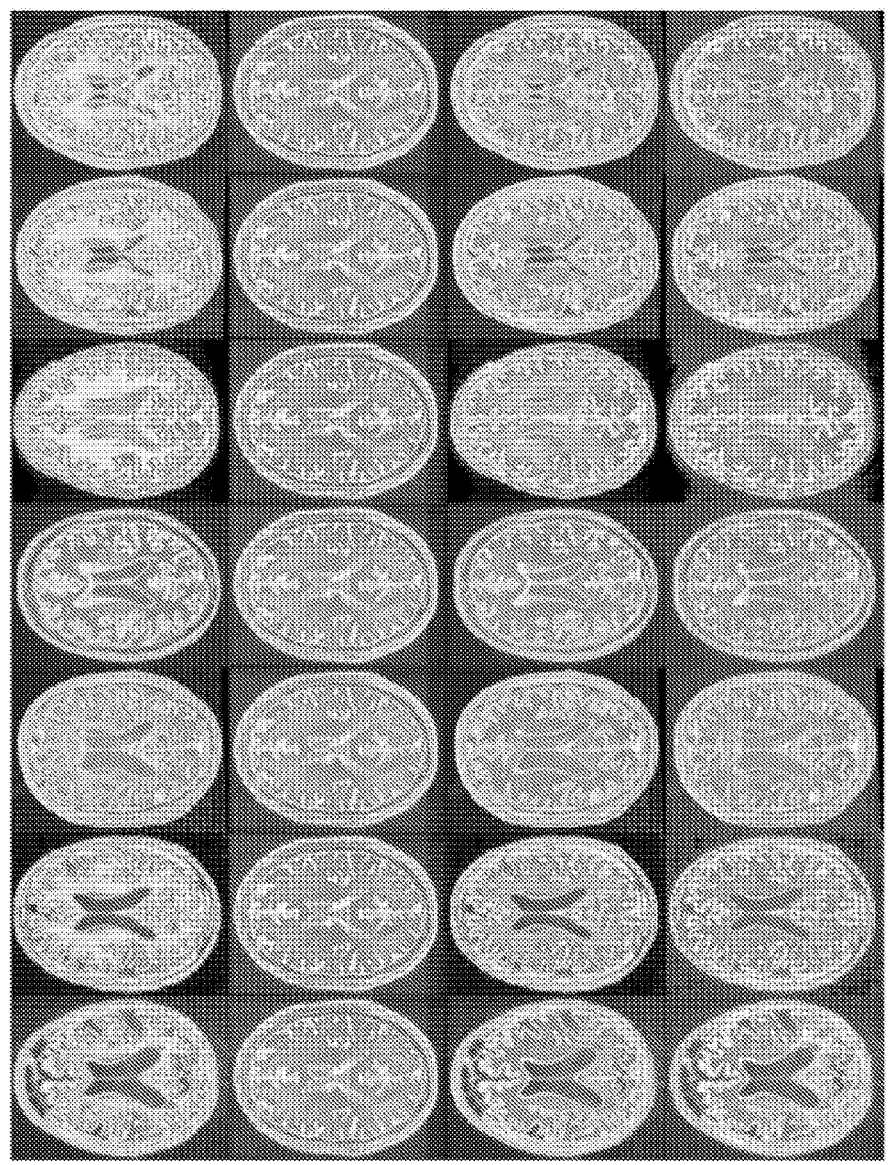
FIG. 11 shows images of the ADNI dataset, sorted according to MAE percentiles (A) 100, (B) 90, (C) 75, (D) 50, (E) 25, (F) 10 and (G) 0 obtained for the foreground voxel set with STI. Images (A) and (G) correspond respectively to the highest (worst) and lowest (best) MAE obtained in the foreground for STI.

FIGS. 10 and 11 present ADNI images sorted according to MAE percentiles 100 (A), 90 (B), 75 (C), 50 (D), 25 (E), 10 (F) and 0 (G) for the foreground voxel set. Images (A) and (G) thus give the highest (worst) and lowest (best) MAE, respectively, for $L_4$ (FIG. 10) and STI (FIG. 11). From top to bottom: input images, standard image, and images standardized with $L_4$ and STI, respectively.

TABLE 3

MAE (%) of the ADNI images presented in FIGS. 4 and 5, obtained for the foreground, WM and GM. Best (lowest) MAE values are highlighted in bold characters.

| Figure | Voxel Set | Tech. | (A) | (B) | (C) | (D) | (E) | (F) | (F) |
|---|---|---|---|---|---|---|---|---|---|
| FIG. 10 | Foreground | Original | 21.27 | 13.93 | 11.94 | 12.14 | 9.90 | 8.85 | 7.87 |
| | | $L_4$ | 11.07 | 9.84 | 9.41 | 9.02 | 8.62 | 8.30 | 7.50 |
| | | STI | 9.93 | 9.71 | 9.24 | 8.81 | 8.69 | 8.48 | 7.56 |
| | WM | Original | 27.89 | 16.65 | 12.90 | 11.28 | 6.88 | 5.08 | 4.04 |
| | | $L_4$ | 8.60 | 7.05 | 6.32 | 4.59 | 4.19 | 5.04 | 3.67 |
| | | STI | 4.42 | 4.86 | 4.03 | 4.04 | 4.40 | 4.34 | 3.64 |
| | GM | Original | 22.61 | 14.31 | 11.24 | 10.77 | 7.58 | 7.20 | 5.62 |
| | | $L_4$ | 9.99 | 8.58 | 7.52 | 6.65 | 6.04 | 6.70 | 4.97 |
| | | STI | 8.75 | 8.05 | 7.03 | 6.50 | 6.43 | 6.50 | 5.31 |
| FIG. 11 | Foreground | Original | 12.14 | 11.77 | 10.10 | 10.90 | 10.13 | 10.29 | 8.93 |
| | | $L_4$ | 10.64 | 9.70 | 8.88 | 8.92 | 8.77 | 8.24 | 7.67 |
| | | STI | 12.05 | 10.11 | 9.60 | 9.05 | 8.57 | 8.23 | 7.32 |
| | WM | Original | 8.04 | 9.38 | 5.34 | 10.01 | 7.68 | 8.30 | 6.43 |
| | | $L_4$ | 6.49 | 5.26 | 6.32 | 5.70 | 4.95 | 4.28 | 4.02 |
| | | STI | 8.24 | 5.94 | 5.00 | 4.11 | 4.89 | 4.32 | 3.69 |
| | GM | Original | 10.72 | 10.00 | 8.30 | 9.21 | 8.59 | 8.19 | 7.37 |
| | | $L_4$ | 8.99 | 7.63 | 7.71 | 6.83 | 6.90 | 6.23 | 5.89 |
| | | STI | 10.59 | 8.12 | 7.69 | 6.70 | 6.79 | 6.29 | 5.49 |

Qualitatively, although foreground MAE decreases from (A) to (G), a corresponding improvement in WM is not necessarily observed. This is also shown in Table 3, where foreground, WM and GM MAE values are given for each image of FIGS. 10 and 11. MAE values for GM do not necessarily follow the trend for the foreground either.

Interestingly, as shown in Table 3, $L_4$ and STI can both result in higher (worse) MAE than with no standardization (see FIG. 11 (A) and (C) for WM). In other words, the WM intensity of the non-standardized image, in these cases, is closer to the standard than the WM intensity given by $L_4$ and STI.

Finally, for the images presented in FIGS. 10 and 11, Table 3 reveals that STI gave the lowest MAE values in 26 cases (foreground: 7, WM: 10, GM: 9) vs. 16 for $L_4$ (foreground: 7, WM: 4, GM: 5). It must be noted that this sample is not representative of the whole ADNI dataset, as we artificially selected images to display at each MAE percentiles for each standardization technique.

Figures 12A, 12B, 12C:
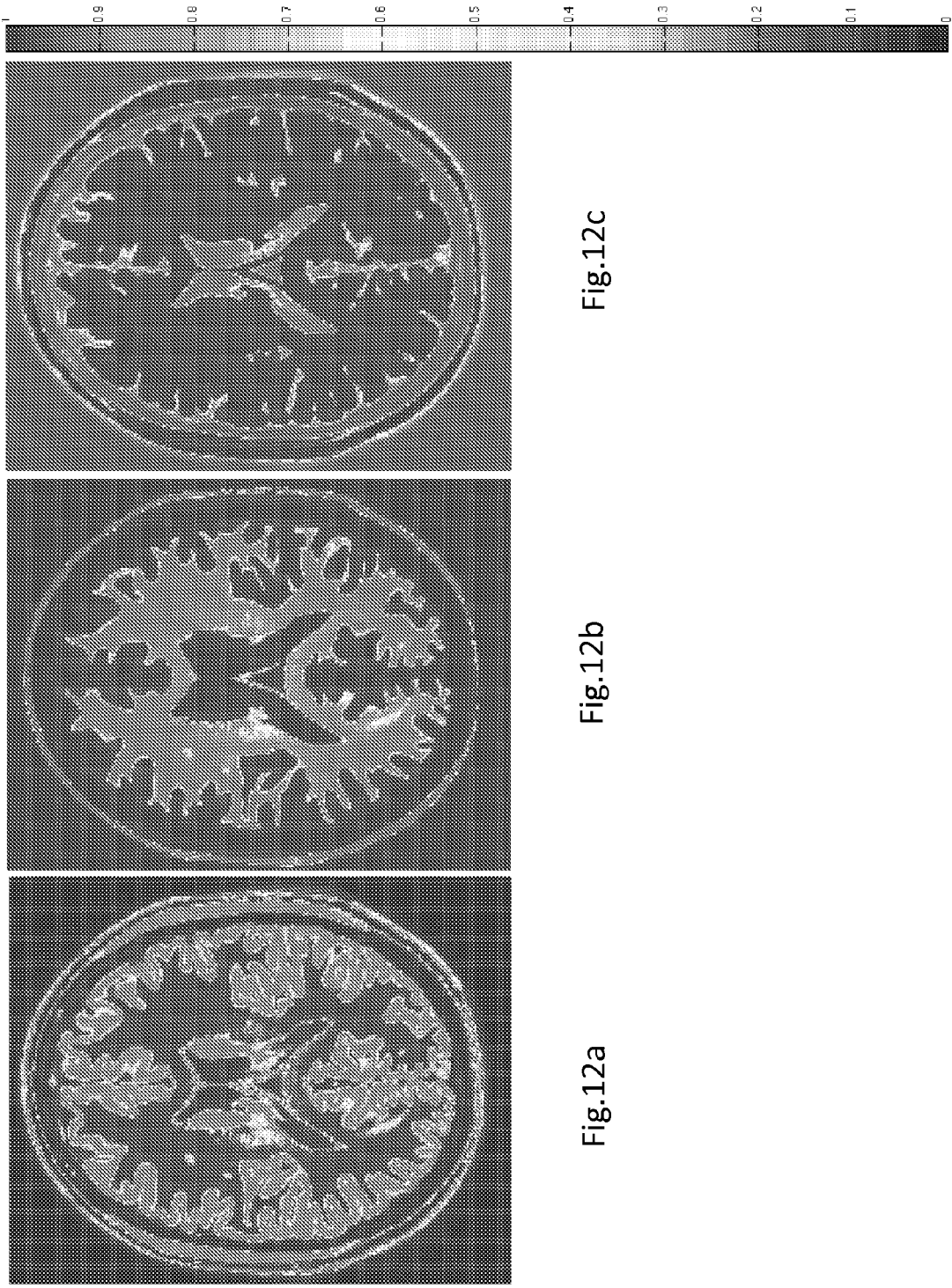
FIG. 12 (a) shows an image of grey matter generated with fuzzy logic classification algorithms.

In some embodiments, fuzzy logic can be exploited to generate tissue-specific masks using classification algorithms. In other embodiments fuzzy logic classification [M. Ozkan, B. M. Dawant, and R. J. Maciunas, "Neural-network-based segmentation of multi-modal medical images: A comparative and prospective study," IEEE Trans. Med. Imag., vol. 12, pp. 534-544, September; and Zijdenbos, A P, Dawant B M, Margolin R A, Palmer A C "Morphometric Analysis of White Matter Lesions in MR images: Methods and Validation", IEEE Trans. Med. Imag., Vol. 13, NO. 4, December 1994], can be used at the end of the processing pipeline whereby, after being processed, each image is fed to a fuzzy classification algorithm. The resultant classification gives a probability map for each tissue (e.g. CSF, GM and WM), with each voxel value ranging from 0 to 1. Examples are presented in FIG. 12 for GM (a), WM (b) and CSF (c), respectively. This procedure yields to a standardization of intensities for each tissue, intensity values being on a same common scale (0 to 1), and, in addition to providing a useful unit of measure, provides images with better overall intensity standardization.

In some embodiments of the present invention, "Background" is included as a tissue type for the purpose of this application. It will be understood that background is not really a tissue type but rather the absence of any other tissue.

STI uses spatial correspondence and joint intensity histograms between the input and standard images to find modes and use them as landmarks in the intensity mapping function. As demonstrated in this study, using spatial correspondence improves the standardization quality.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

What is claimed is:

1. A method of standardizing intensity of a medical image comprising: registering said medical image to a standard image; applying one or more masks to said medical and said standard images for isolating image components; determining the most common intensity data pair between said medical image and said standard image for each isolated image component; calculating a formula, wherein said formula is of a linear, polynomial and basis-function formula, and wherein said basis-function formula is one of a Guassian, Bessel, Sine and Cosine formula, that joins the most common intensity data pair of each image component; and interpolating an intensity data adjustment using said formula and applying it to said medical image data to generate a standardized version of said medical image.

2. The method of claim 1, further comprising establishing at least one of a minimal and maximal data pair between test and standard images, wherein said minimal and/or maximal data pair allows for more precise intensity data interpolation.

3. The method of claim 1, further comprising pre-processing said medical image.

4. The method of claim 3, wherein said pre-processing comprises one or more of filtering, intensity heterogeneity correction, de-noising, re-sampling, smoothing, scaling and clamping.

5. The method of claim 1, wherein said medical image is an MRI image.

6. The method of claim 5, wherein said MRI image is a brain image.

7. The method of claim 6, wherein said brain image is from a patient suffering from Alzheimer's disease.

8. The method of claim 1, wherein said image component is a tissue type.

9. The method of claim 8, wherein said tissue type is one of grey matter, white matter, cerebro-spinal fluid and background.

10. The method of claim 1, wherein said mask is a tissue-specific mask.

11. The method of claim 1, further comprising converting said intensity value into a probability value of being a tissue type using a fuzzy logic classification algorithm.

12. A method of determining a disease risk factor or of performing classification of an image comprising: receiving an unstandardized image; standardizing said image according to claim 1; and determining a disease risk factor or performing classification using said standardized image.

13. An apparatus for standardizing intensity of a pre-processed medical image to a standard image comprising:
an image registrator for registering said medical image to said standard image;
a component isolator for isolating specific image components;
a data pair frequency selector for selecting the highest frequency intensity data pair;
an intensity adjustment calculator adapted to calculate a formula, wherein said formula is one of a linear, polynomial and basis-function formula, and wherein said basis-function formula is one of a Guassian, Bessel, Sine and Cosine formula, that joins the most common intensity data pair of each image component;
an intensity adjuster for adjusting the intensity data of said medical image using said formula to generate a standardized version of said medical image.

14. The apparatus of claim 13 further comprising a visual display for presenting standardized images.

15. The apparatus of claim 13 further comprising a transmitter for transmitting said data to another location.

16. The apparatus of claim 13 wherein the component isolator is a tissue-specific mask.

17. The apparatus of claim 13 wherein said pre-processed medical image is obtained by scaling the image.

18. The apparatus of claim 13 wherein said pre-processed medical image is obtained by one or more of filtering, de-noising, heterogeneity correction, re-sampling, smoothing.

19. A system for automatically calculating a disease risk factor or medical classification based on a medical image comprising:
a standardization apparatus as claimed in claim 13; and
a calculator configured to process said standardized image to generate said disease risk factor or medical classification.

* * * * *